United States Patent [19]

Ito et al.

[11] Patent Number: 4,589,568
[45] Date of Patent: May 20, 1986

[54] PACKAGE

[75] Inventors: Hideyuki Ito, Fuji; Nobuyasu Takanashi, Yamanashi, both of Japan

[73] Assignee: Terumo Corp., Tokyo, Japan

[21] Appl. No.: 597,441

[22] Filed: Apr. 6, 1984

[30] Foreign Application Priority Data

Apr. 23, 1983 [JP] Japan ................................. 58-71992

[51] Int. Cl.$^4$ ............................................. B65D 41/00
[52] U.S. Cl. ...................................... 220/359; 229/43
[58] Field of Search .................. 220/359, 319; 229/43, 229/5.5

[56]         References Cited
        U.S. PATENT DOCUMENTS

| 3,391,847 | 7/1968 | Christine et al. | 220/359 |
| 3,525,454 | 8/1970 | Frederiksen | 220/359 |
| 3,561,668 | 9/1971 | Bergstrom | 220/359 |
| 3,892,351 | 7/1975 | Johnson et al. | 220/359 |
| 4,044,941 | 8/1977 | Knudsen | 220/359 |
| 4,207,989 | 6/1980 | Ingemann | 220/359 |
| 4,378,074 | 3/1983 | Brochman | 220/359 |
| 4,482,053 | 11/1984 | Alpern et al. | 220/359 |

FOREIGN PATENT DOCUMENTS

| 0033824 | 8/1981 | European Pat. Off. | 220/359 |
| 1747781 | 6/1957 | Fed. Rep. of Germany . | |
| 2411681 | 7/1975 | Fed. Rep. of Germany . | |
| 80/02412 | 5/1979 | Int'l Pat. Institute | 220/359 |

*Primary Examiner*—Joseph Man-Fu Moy
*Attorney, Agent, or Firm*—Frishauf, Holtz, Goodman & Woodward

[57]            ABSTRACT

A package obtained by superposing a sheetlike lid through the medium of a hot melt layer, on a tray provided along the edge of a recess therein with a sheetlike flange part, and then heat sealing the tray and the sheetlike lid at the sheetlike flange part. The heat sealed portion formed between the sheetlike flange part of the tray and the sheetlike lid includes at least one primary joined portion having one of the sheetlike parts strongly pressed down and partially buried in the other sheetlike part, and at least one secondary joined portion adjacent said primary joined portion having said sheetlike parts pressed down less strongly against each other than in the primary joined portion. The secondary portion is at least on the inner side of the primary joined portion toward the tray recess, relative to the direction of the cross section of the heat sealed portion, thus serving to provide protection for the primary joined portion.

13 Claims, 12 Drawing Figures

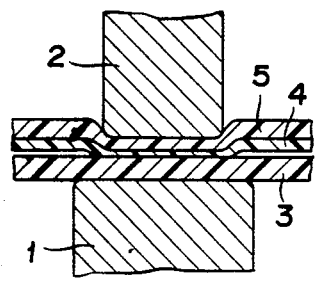
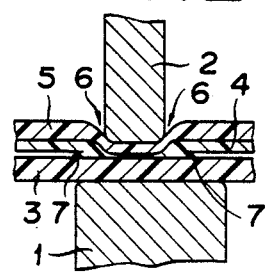
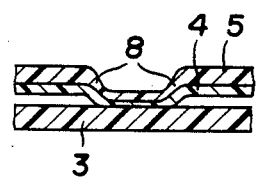
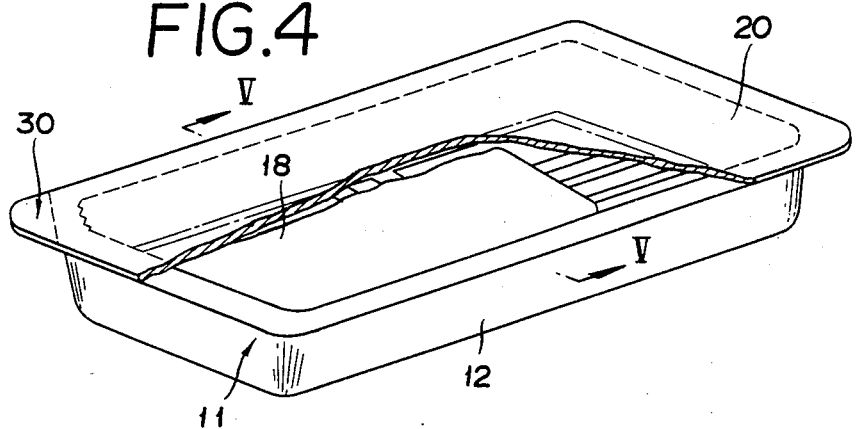
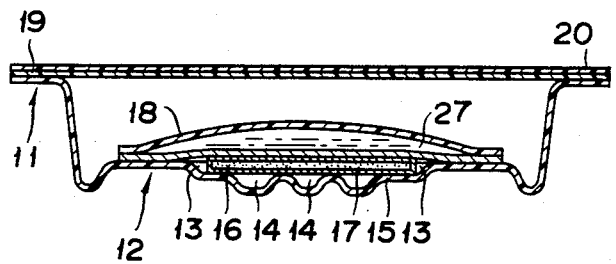

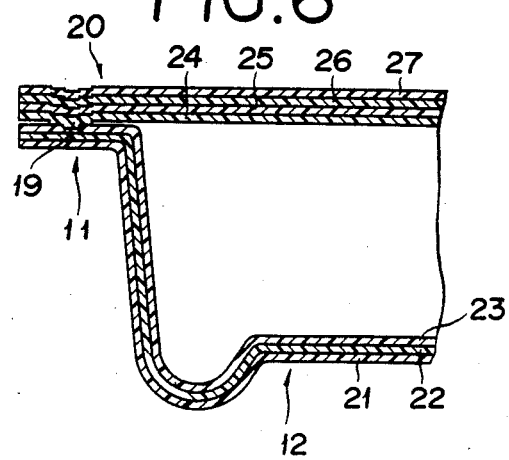
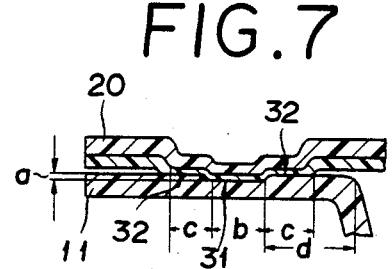
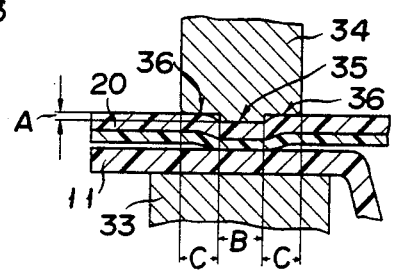
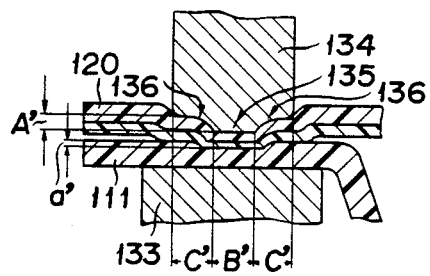
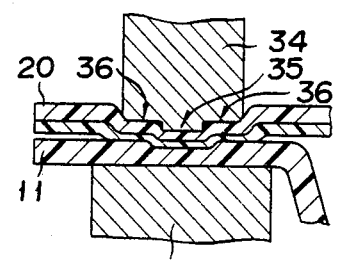
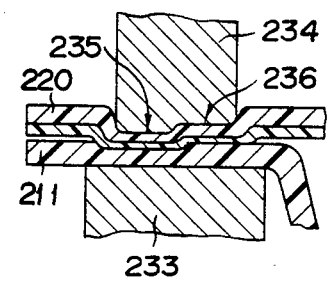
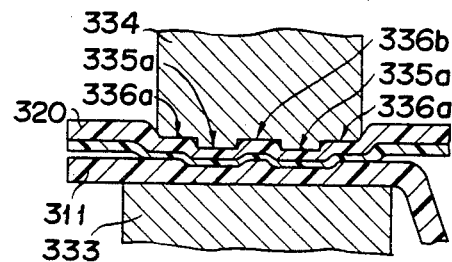

PACKAGE

BACKGROUND OF THE INVENTION

1. Field of the Invention

This invention relates to a package for accommodating and preserving medical devices, medical containers such as blood bags, containers containing solution administration, medicines, transintestinal nutrient foodstuffs and other various articles directly or after accomodating other containers and to a method for the manufacture thereof. More particularly, this invention relates to a package incorporating a stably sealed part and to a method for the manufacture thereof.

2. Description of Prior Arts

Most packages used for accommodating and preserving various articles or substances as described above have their peripheral edges sealed by heating with hot metal dies, high-frequency induction heating or ultrasonic heating. The heat sealing of the peripheral edge of a given package is accomplished, for example as ilustrated in FIG. 1, by interposing between a lower metal die 1 and a heat sealing upper metal die 2, a lower sheet 3 and an upper sheet 5 having a hot melt layer 4 superposed or deposited on the lower sheet 3 side surface thereof and placed on top of the lower sheet 3, and subsequently pressing the upper metal die 2 down against the lower metal die 1 thereby fusing the two sheets 3, 5 along the peripheral edges thereof. The heat sealing upper metal die 2 conventionally used for this heat sealing usually has a land or flat surface.

When the upper metal die 2 has a land of large width as illustrated in FIG. 1, however, a force of fixed magnitude used by the upper metal die 2 in pressing the sheets produces a small pressure per unit area because of the large surface area of the land. Consequently, the peripheral edge of a finished package is sealed with insufficient strength such that it will readily separate under the influence of some external force.

When the upper metal die 2 has a land of small width as illustrated in FIG. 2, since the land has a small surface area, the pressure exerted by the upper metal die 2 per unit area is large so that the peripheral edges of the lower sheet 3 and the upper sheet 5 are joined with ample strength. Because of the small area of contact, however, the overall sealing strength to be produced is not sufficient and, moreover, the thickness of the upper sheet 5 is decreased along the peripheral edge 6 thereof which is subjected to the heat sealing. Thus, the heat sealed edge of a finished package has poor resistance to impacts and is liable to separate when the package is subjected to a drop test. Since the hot melt material in a fused state finds no room in the metal dies for its escape, there is a possibility that some of the fused hot melt material will find its way between and beyond the external bounds of the upper sheet 5 and the lower sheet 3 and stick out in the form of burrs 7. In the case of the sheet 5 on the heat sealing upper metal die 2 side, the portions of the upper sheet 5 which hit against the peripheral corners of the heat sealing upper metal die 2 form thin weak portions 8 as illustrated in FIG. 3. In an extreme case, these portions 8 may sustain pinholes. The occurrence of burrs as in the former case entails a problem that such burrs impair the appearance of the finished package. The occurrence of thin weak portions occasionally accompanied by pinholes as in the latter case entails a more serious problem, in that the finished container becomes incapable of safely preserving its contents and suffers from ready separation of the upper sheet. When the package is intended for a medical device or a medicine and, therefore, is required to ensure perfect isolation of its interior from the ambient air, the problem involved in the latter case will prove to be a fatal defect. Particularly when the package contains a medical container such as a blood bag or gh transfusion bag or a medical device, it weights heavily in itself. The sealed portion of the package, therefore, is exposed to a fairly large amount of stress when the bottom thereof sags down or when the package is dropped onto a solid surface. At times, this stress may be so high as to inflict breakage to the sealed portion of the package.

OBJECT OF THE INVENTION

An object of this invention, therefore, is to provide a novel package and a method for the manufacture thereof.

Another object of this invention is to provide a package possessed of a stable sealed portion and a method for the manufacture thereof.

Yet another object of this invention is to provide a package which enjoys high seal strength, offers outstanding resistance to impacts, produces no burr, entails no occurrence of thin wall or pinhole in the sealed edge, and yet excels in the ease with which the sealed edge is opened for removal of its contents, and a method for the manufacture thereof.

SUMMARY OF THE INVENTION

The objects described above are accomplished by providing a package produced by superposing a sheetlike lid through the medium of a hot melt layer, on a tray member provided along the edge of a recess therein with a sheetlike flange part, and then heat sealing the tray member and the sheetlike lid at the sheetlike flange part. The heat sealed portion formed between the sheetlike flange part of the tray member and the sheetlike lid is comprised of at least one primary joined portion having one of the aforementioned sheetlike parts strongly pressed down and partially buried in the other sheetlike part, and at least one secondary joined portion adjacent said primary joined portion having the sheetlike parts pressed down less strongly adjacent each other than in the primary joined portion. The secondary portion is at least on the inner side of the primary joined portion toward the tray recess, relative to the direction of the cross section of the heat sealed portion, thus serving to provide protection for the primary joined portion.

This invention embraces a package which has two secondary joined portions formed one each on the opposite sides of the primary joined portion. It also embraces a package which has one primary joined portion and preferably has secondary joined portions on the opposite sides of the primary joined portion. It further embraces a package which has one of the two sheetlike parts partially buried into the other sheetlike part at a depth of at least 0.05 mm. Further, the invention embraces a package which has the partial burying at a depth in the range of 0.1 to 0.4 mm. It also embraces a package which has the inner edge of the primary joined portion separated by a distance of at least 0.5 mm from the edge of the internal surface of the wall of the tray member. It further embraces a package wherein the distance intervening between the inner edge of the primary joined portion and the edge of the internal surface of the wall of the tray member is at least 1 mm. The invention also embraces a package which has a hot melt layer superposed or spread on the sheetlike lid. It further embraces a package which has two primary joined portions formed parallelly to each other. This invention embraces a package wherein the tray member is made of a sheet formed by superposing a layer of polyolefin through the medium of a layer pervious to gas and steam on a layer of polyolefin, the lid is made of a sheet formed by sequentially superposing a layer of polyamide, a layer pervious to gas and steam, and a layer resistant to the heat used in the heat sealing, and the hot melt material is superposed or spread on the aforementioned layer of polyamide. It also embraces a package wherein the tray member has the layer of polyolefin formed of polypropylene and the hot melt material is a blend of polyethylene with polypropylene. It further embraces a package wherein the lid is removable from the tray member by peeling.

The aforementioned objects are accomplished by this invention providing a method for the manufacture of a package, comprising the steps of superposing a sheetlike lid through the medium of a hot melt layer on a tray member provided along the edge of a recess therein with a sheetlike flange part and then heat sealing the tray member and the sheetlike lid, and including nipping the sheetlike flange part of the tray member and the sheetlike lid between (1) a heat sealing metal die provided with at least one primary press part formed with a leading end and a secondary press part formed adjacent to said primary press part on the side of the tray recess and having a leading end slightly shorter than the leading end of the primary press part, and (2) a metal die of a flat surface disposed as accurately matched to the heat sealing metal die, and subsequently pressing the sheetlike flange part and the sheetlike lid between the aforementioned two metal dies.

Further, this invention embraces a method which uses a heat sealing metal die having two secondary press parts formed one each on the opposite sides of the primary press part. It also embraces a method which uses a heat sealing metal die having one primary press part and preferably two secondary press parts formed one each on the opposite sides of the primary press part. It further embraces a method wherein the heat sealing metal die is pressed down from the sheetlike lid side. The invention embraces a method wherein the secondary press part is a curved surface continuing into the leaing end of the primary press part. It also embraces a method wherein the distance from the leading end of the secondary press part to the leading end of the primary press part is in the range of 0.05 to 5 mm, preferably 0.1 to 0.4 mm. It further embraces a method wherein the distance from the shortest section of the secondary press part to the leading end of the primary press part is in the range of 0.05 to 0.4 mm. Further this invention embraces a method wherein the width of each of the primary press parts is 0.05 to 5 mm, preferably 0.1 to 0.04 mm and the width of each of the secondary press parts is 0.1 to 10 mm, preferably 0.1 to 5 mm. It also embraces a method wherein two primary press parts are disposed parallelly to each other. It further embraces a method wherein the heat sealing metal die is pressed down from the sheetlike flange side of the tray member.

BRIEF DESCRIPTION OF THE DRAWINGS

FIGS. 1 and 2 are cross sections illustrating a conventional heat sealing method, FIG. 3 is a cross section illustrating a typical portion heat sealed by the conventional method, FIG. 4 is a partially cutaway perspective view illustrating a typical package according to the present invention, FIG. 5 is a cross section taken along the line V—V in the diagram of FIG. 4, FIG. 6 is a partially enlarged cross section illustrating a heat sealed part, FIG. 7 is an exaggerated enlarged cross section illustrating one embodiment of the formation of the heat sealed part of a package according to the present invention, FIGS. 8 and 9 are cross sections illustrating different steps in the formation of the heat sealed part of FIG. 7, FIG. 10 is a cross section illustrating another embodiment of the formation of the heat sealed part of a package according to the present invention, FIG. 11 is a cross section illustrating yet another embodiment of the formation of the heat sealed part of a package according to the present invention, and FIG. 12 is a cross section illustrating a further embodiment of the formation of the heat sealed part of a package according to the present invention.

PREFERRED EMBODIMENT OF THE INVENTION

Now, the package of the present invention will be described in detail below with reference to the accompanying drawings. In the following description, a package intended to accommodate and preserve a medical container will be depicted by way of illustration. This invention is not limited to this particular package.

The expression "heat seal" as used in this invention refers to an operation for thermally fusing two members through the medium of a hot melt material. As means for effecting this thermal fusion, there may be cited heating by the use of hot metal dies, high-frequency induction heating, and ultrasonic heating. The expression "thickness of the joined part" as used in this invention refers to the sum of the thickness of the flange part of the tray member, the thickness of the hot melt layer, and the thickness of the sheetlike lid as measured in the joined part of the package.

A package for the storage of a medical container according to this invention includes a tray part 12 provided round the opening thereof with a flange portion 11, having a recess portion 13 for receiving a deoxidizer 17 formed in at least one side thereof if necessary, for example, the bottom side, and further at least one groove 14 formed in the bottom portion of the recess portion as illustrated in FIGS. 4–6. Within this deoxidizer receiving portion 13, the deoxidizer 17 covered on at least one side thereof with a gas-impervious sheet 15 such as aluminum foil, synthetic resin film, paper or cloth impregnated or coated with wax or synthetic resin and on at least one other side thereof, generally the side opposite the aforementioned side, with a gas-previous sheet 16 such as paper or cloth, is received in such a manner that the gas-previous sheet 16 is positioned on the groove 14 side. The groove 14 is formed so as to reach the outside of the deoxidizer receiving portion 13 and form a free passage for gases. After the deoxidizer 17 and a medical container 18 have been set in position within the tray part 12, a lid 20 is heat sealed through the medium of the hotmelt adhesive layer 19 to the tray part 12 to be peeled open later.

In the package of the present invention for the storage of the medical container, any of materials which are capable of providing a barrier to passage of gases and steam and are highly heat sealable can be used for the tray part 12 and the lid member 20. Examples are shown below. They are particularly excellent in shape-retaining property, ability to bar passage of gases and steam and heat sealability, and are transparent. As illustrated in FIG. 6, the tray part 12 is produced by molding in the shape of a tray a laminated sheet comprising a polyolefin layer (outer layer) 21, a layer capable of barring passage of gases and steam (intermediate layer) 22 and a polyolefin layer (inner layer) 23. The lid 20 is formed by laminating a polyamide layer (inner layer) 24, a layer capable of barring passage of gases and steam (intermediate layer) 25 and a layer possessed of thermal resistance enough to withstand the conditions of heat sealing (outer layer) 26. The hotmelt adhesive layer 19 is formed of a blend of polyethylene with polypropylene.

Examples of the polyolefin which forms the outer layer 21 and the inner layer 23 of the tray part 12 are polyethylene and polypropylene. Polypropylene is preferred because of its excellence in shape-retaining property and thermal resistance over polyethylene. To be used advantageously herein, the polyethylene is required to have a molecular weight of 3,000 to 200,000, preferably 50,000 to 100,000, and the polypropylene to have a molecular weight of 5,000 to 1,000,000, preferably 100,000 to 500,000. The thickness of each of the polyolefin layers is 500 to 600 $\mu$m. The intermediate layer 22 of the tray part 12 which is capable of barring passage of gases and steam is desired to be formed of ethylene-vinyl alcohol copolymer. The thickness of this layer is about 50 $\mu$m. The vinyl alcohol content of the copolymer is desired to be 20 to 80 mol%, preferably 40 to 70 mol%. The molecular weight of the copolymer is desired to be 5,000 to 100,000, preferably 10,000 to 50,000.

The hotmelt layer constituting the inner layer 24 of the lid member 20 is desired to be formed of a blend of polyethylene with polypropylene. The weight ratio of the polyethylene to the polypropylene in the blend, when the outer layer 21 of the tray part 12 is made of polypropylene, is desired to fall in the range of 20:80 to 50:50 from the standpoint of both heat sealability and peel openability of the tray part. The thickness of the inner layer 24 is 30 to 60 $\mu$m, preferably 40 to 50 $\mu$m. This layer of the blend is superposed by a layer of polyamide, such as, for example, a layer of nylon 6 or nylon-6,6. This nylon layer permits the lid member to retain its strength. The intermediate layer 25 which is capable of barring passage of gases and steam is desired to be formed of polyvinylidene chloride or ethylene-vinyl alcohol copolymer. Generally, polyvinylidene chloride is used as superposed on a polyolefin film, particularly a biaxially drawn polypropylene film. Generally the molecular weight of the polyolefin is 5,000 to 1,000,000 preferably 100,000 to 500,000. The thickness of the polyolefin film is 20 to 40 $\mu$m. The molecular weight of the aforementioned polyvinylidene chloride is 8,000 to 20,000, preferably 10,000 to 15,000, and the thickness of the polyvinylidene chloride film is 5 to 10 $\mu$m. This film exhibits an outstanding ability to bar passage of gases and steam. A still better barrier property is obtained by using a plurality of such layers capable of barring passage of gases and steam in a superposed form. To ensure safe storage of a plastic medical container holding a medicinal fluid therein, the intermediate layer 25 is desired to have not more than 1 g/m$^2$.24 hr (40° C., 90% RH), preferably 0.1–0.2 g/m$^2$.24 hr (40° C., 90% RH), of perviousness to humidity. To ensure prevention of growth of aerobic microorganisms, the gas barrier property of the intermediate layer 25 is desired to be not more than 0.1%/72 hr, preferably not more than 0.1%/50 hr of oxygen concentration within the package. Examples of a resin of the outer layer which is possessed of thermal resistance enough to withstand the conditions of heat sealing, include polyesters such as polyethylene teraphthalate and polybutylene teraphthalate, polyamides such as nylon 6 and nylon 6,6 and polypropylene. Among the polymers mentioned above, polyethylene teraphthalate proves to be particularly desirable. The thickness of the outer layer is 10 to 30 $\mu$m, preferably 12 to 25 $\mu$m.

The weight ratio of the polyethylene to the polypropylene in the hotmelt adhesive layer is from 20:80 to 50:50 where the inner layer 23 of the tray part 12 is formed of polypropylene and from 80:20 to 50:50 where the inner layer 23 is formed of polyethylene. This is because the seal is peeled open with great difficulty when the proportion in the blend of the material identical with the polyolefin forming the inner layer of the tray part 12 is too high and the adhesiveness of the flange portion and the lid member is insufficient when the proportion is too low.

In the package which is not required to be pervious to gas and steam, neither the tray part 12 nor the lid 20 is required to be provided with a layer pervious to gas and steam. In this package, the tray part 12 and the lid 20 are only required to be formed of materials capable of being heat sealed.

In the package of the present invention, the heat sealed part to be formed between the flange part 11 of the tray part 12 and the lid 20 consists of a primary joined part 31 and one secondary joined part 32 formed on the inside of the primary joined part 31, or two secondary joined parts 32 formed one each on the opposite sides of the primary joined part 31 as illustrated in an exaggerated manner in the partially enlarged diagram of FIG. 7. In the aforementioned primary joined part 31, because of the strong pressure exerted by the metal dies during the course of heat sealing, the hot melt material is fused and, at the same time, a depression is formed in the flange part 11, and the lid 20 is partly buried in this depression. Thus, the primary joined part 31 generally has a wall thickness slightly less than any other part. The secondary joined part 32 on one side or on either side of the primary joined part 31 is formed by causing parts of the materials of the lid 20 and the flange part 11 fused or softened in the primary joined part 31 to flow out and, by virtue of capillary action, fill up the gap between the partly fused parts of the lid and the flange part. Thus, the secondary joined part 32 has been pressed less strongly and consequently finished in a large wall thickness. Unlike the conventional package, the package produced by this invention neither produces any burr nor suffers occurrence of a thin wall near the sheet-joined part as illustrated in FIG. 3.

The depth of the aforementioned depression is at least 0.05 mm. Preferably, it is in the range of 0.1 to 0.4 mm. If this depth is less than 0.05 mm, then the depression is insufficient and the sealing strength is consequently insufficient. When this depth falls in the range of 0.1 to 0.4 mm, the sealing strength is ample. The width b of the primary joined part 31 generally falls in the range of 0.1 to 10 mm, preferably 0.1 to 5 mm. The width c of the secondary joined part 32 generally falls in the range of 0.1 to 10 mm, preferably 0.5 to 5 mm. The distance d between the edge of the internal surface of the wall of the tray part to the inner edge of the primary joined part is at least 0.5 mm and preferably at least 1 mm. It preferably falls in the range of at least 2 mm. If this distance d is less than 0.5 mm, then the secondary joined part 32 loses significance as though it were completely absent from the beginning. As the result, the portion of small wall thickness occurs all along the boundary and offers insufficient resistance to impacts.

Now, the method to be adopted for the manufacture of a package of the construction described above will be explained with reference to FIGS. 8 and 9. Specifically, this package is manufactured by heat sealing the flange part 11 of the tray part 12 and the sheetlike lid 20 by the use of metal dies constructed as illustrated in FIGS. 8 and 9. The lower metal die 33 is applied to the lower side of the flange part 11 and the heat sealing upper metal die 34 is pressed down against the upper side of the lid 20. The heat sealing upper metal die 34 is disposed along the aforementioned flange part 11 and, as plain in the cross sectional shape illustrated in FIG. 8, is provided with at least one primary press part 35 (one in FIG. 8) having a flat leading end and one secondary press part 36 disposed at least on the inner side of the primary press part (one each on either side in FIG. 8) and having a slightly shorter leading end (of flat surface, for example) than the primary press part. In this heat sealing upper metal die 34, the distance A between the leading end of the secondary press part 36 and the leading end of the primary press part 35 falls in the range of 0.05 to 5 mm, preferably in the range of 0.1 to 0.4 mm. The width B of each primary press part 35 is in the range of 0.1 to 10 mm, preferably in the range of 0.1 to 5 mm. The width C of each secondary press part 36 is in the range of 0.1 to 10 mm, preferably in the range of 0.1 to 5 mm. Just one primary press part 35 does not always suffice. Any number of primary press parts may be used to suit the particular occasion. Further, the primary press part is not limited to the one shown in the drawing, but it may be a triangle shape projected to lower portion in cross section.

When the lid 20 and the flange part 11 are pressed by the heat sealing upper metal die 34 and the lower metal die 33 as illustrated, since the primary press part 35 protrudes from the secondary press part 36 as shown in FIG. 9, they are pressed more strongly below the primary press part 35 than below the secondary press parts 36. By the heat of the metal dies, the hot melt material is fused and, at the same time, the materials of the lid 20 and the flange part 11 are partly softened. By virtue of the pressure mentioned above, the flange part 11 is depressed in the portion corresponding to the primary press part 35 and the lid 20 is partially buried in the depression so formed in the flange part 11. In this case, the pressed portion often acquires a slightly smaller wall thickness than at any other portion. Under the secondary press part 36, the lid 20 and the flange part 11 are pressed less strongly than under the primary press part 35. The pressed portion in this case, therefore, frequently acquires a slightly larger wall thickness than at the portion pressed by the primary press part 35. Consequently, the lid 20 and the flange part 11 of the tray member 12 are evenly and safely joined without suffering otherwise possible occurrence of a thin weak wall or pinholes.

FIG. 10 represents another embodiment of this invention. In the heat sealing upper metal die 134, the primary press part 135 formed at the center has a flat surface and the secondary press parts 136 formed one each on the opposite sides of the primary press part have curved surfaces continuing into the leading end of the primary press part 135. In this case, the depth a' of the depression is equal to the depth a of the depression shown in FIG. 7. The widths of each primary press part and each secondary press part are equal to the widths of the corresponding parts shown in FIG. 7. The distance between the edge of the internal surface of the wall of the tray member and the inner edge of the primary press part is also equal to the distance between the corresponding edges shown FIG. 7. The distance A' between the shorter section of the secondary press part 136 and the leading end of the primary press part 135 falls in the range of 0.05 to 5 mm, preferably in the range of 0.1 to 0.4 mm. Then, the width B' of each primary press part 135 and the width C' of each secondary press part 136 are equal to the corresponding widths shown in FIG. 8. In FIG. 10, the numerical symbols which are sums of the numerical symbols of FIGS. 7-9, plus 100, denote like parts.

FIG. 11 depicts yet another embodiment of this invention. This embodiment represents a case wherein only one secondary press part 236 is disposed on the inner side of the primary press part 235. In FIG. 11, the numerical symbols which are sums of the numerical symbols of FIGS. 7-9, plus 100, denote like parts.

FIG. 12 depicts a further embodiment of the present invention. This embodiment represents a case wherein two primary press parts 335a, 335b are disposed parallelly to each other and two secondary press parts 336a are disposed on the outer sides of the primary press parts and one secondary press part 336b is disposed between the primary press parts. In FIG. 12, the numerical symbols which are sums of the numerical symbols of FIGS. 7-9, plus 300, denote like parts.

In any of the embodiments described so far, the heat sealing upper metal die is pressed from the lid side. Alternatively, it may be pressed from the side of the flange part of the tray member to form the depression in the lid.

When the package finished by the heat sealing described above is accommodating a medical container or other similar article, the heat sealed part 19 is required to resist impacts or manifest a gas barrier property when necessary. On the other hand, this heat sealed part 19 is required to be readily separable by peeling to permit removal of the medical container from the package. In the heat sealed part obtained by this invention, the primary joined part formed at the center is produced because the powerfully pressed portions of the materials of the flange part and the lid are fused and joined intimately. By virtue of the pressure, the lid can be partially buried in the flange part of the tray part to ensure the stability of the formed seal. Since the secondary joined part is formed under a slightly smaller pressure, it is opened more readily by peeling than the primary joined part. Thus, the secondary joined part constitutes itself the part for starting the opening of the package. It further serves to prevent the primary joined part form acquiring a wall thickness reduced to an excessive extent and, at the same time, improve the resistance of the joined part to impacts. The openability of the package is sufficient because the tray part and the lid are made of materials which permit ready peeling.

EXAMPLE

A blood bag was set in place inside a tray molded of a laminate consisting of a layer of polypropylene (outer layer) 500 μm in thickness, a layer of ethylene-vinyl alcohol copolymer (intermediate layer) 50 μm in thickness, and a layer of polypropylene (inner layer) 500 μm in thickness. Then, a flat lid produced by laminating a layer of polyamide (inner layer) 15 μm in thickness, a layer of polyvinylidene chloride (intermediate layer) 10 μm in thickness, and a layer of polyethylene terephthalate (outer layer) 20 μm in thickness was heat sealed, through the medium of a layer of polyolefin (a 65:25 mixture of polyethylene and polypropylene) deposited as a hot melt material on the lid, with the tray by the use of metal dies 34 having a land 3 mm in width (width of primary joined part 1 mm and width of each secondary joinded part 1 mm) as illustrated in FIG. 7.

Control 1

The procedure of the example described above was repeated, except that the heat sealing was carried out by the use of metal dies (width 3 mm) as illustrated in FIG. 2.

Control 2

The procedure of the example described above was repeated, except that the heat sealing was carried out by the use of metal dies (width 1 mm) as illustrated in FIG. 2.

In the packages produced as described above, the joined parts had seal strength of 1 to 1.5 kg. These joined parts were tested for peel strength and for strength against impacts of fall. The test for strength against impacts of fall was conducted by dropping a given package from a height of 10 m. Any package which, on landing on the floor, sustained even a slightest peeling in the joined part was reported as one broken. The results were as shown in Table 1.

TABLE 1

|  | Example | Control 1 | Control 2 |
|---|---|---|---|
| Seal strength (kg) | 1–1.5 | 1–1.5 | 1–1.5 |
| Peeling strength (kg) | 3.6 | 6.2 | 3.8 |
| Strength against impacts of fall (number of packages broken/ number of packages dropped) | 0/20 | 0/20 | 3/20 |

From the test results given above, it is noted that the packages produced in the working example of this invention exhibited the smallest yet ample peel strength enough to ensure ready peeling of the joined parts, and sustained no breakage under impacts of fall. These results testify that the present invention provides packages with improvement in peeling strength and strength to withstand breakage under impacts of fall.

The packages manufactured in accordance with this invention are used for the purpose of accommodating and preserving medical devices, medical containers such as the blood bag and the transfusion bag, medicines, foodstuffs, and other articles.

As described above, the present invention provides a package produced by superposing a sheetlike lid through the medium of a hot melt layer, on a tray provided along the edge of a recess therein with a sheetlike flange part, and then heat sealing the tray and the sheetlike lid at the aforementioned sheetlike flange part. The package has a feature that the heat sealed portion formed between the sheetlike flange part of the tray and the sheetlike lid consists of at least one primary joined portion having one of the sheetlike parts strongly pressed down and partially buried in the other sheetlike part, and at least one secondary joined portion on the inner side of the primary joined portion relative to the direction of the cross section of the heat sealed portion for serving to provide protection for the primary joined portion. In the heat sealed part formed between the flange part of the tray and the sheetlike lid, therefore, more powerful adhesion is produced in the primary joined part. In this primary joined part, the lid is partially buried in the flange part or the flange part is partially buried in the lid. Thus, the package is sealed stably.

Where two secondary joined parts formed in a larger wall thickness under less powerful pressure occur, one each on the opposite sides of one primary joined part, they serve to prevent the primary joined part acquiring a wall thickness reduced to an excessive extent and, at the same time, protect the primary joined part from the opposite sides. As the result, the boundaries of the primary joined part are prevented from losing wall thickness and strength or sustaining pinholes, and are enabled to acquire enhanced resistance to impacts.

Since the secondary joined parts are formed under less powerful pressure than the primary joined part, they are peeled more readily than the primary joined part when the package is opened. The initial resistance which the secondary joined parts offer to the peeling is small enough to permit ready opening of the package.

When the package is constructed of the specific laminates described above, the tray enjoys high shape-retaining property and high transparency owing to the attributes of the polyolefin layers constituting the inner and outer layers of the laminate, exhibits an outstanding gas barrier property owing to the imperviousness to gas and steam exhibited by the ethylene-vinyl alcohol copolymer layer, and possesses transparency. Since the lid is constructed as described above, it possesses ample strengh yet permits ready peeling owing to the attributes of the layer of polyamide such as nylon, exhibits high imperviousness to gas and steam owing to the use of a layer impervious to gas and steam such as, for example, the layer of polyvinylidene chloride or the layer of ethylene-vinyl acetate copolymer, and preserves ample shape-retaining property even after heat sealing owing to the use of polyester, polyamide, or polypropylene as the material for the outer layer expected to withstand the heat during the course of heat sealing. Because all of these component layers of the lid are transparent, the lid enables the contents of the package to be clearly inspected from outside. When the polyolefin layer in the laminate of the tray is formed of polypropylene and the polyolefin layer (inner layer) 24 in the laminate of the lid is formed of a hot melt adhesive agent, specifically a blend of polyethylene and polypropylene, and these two polyolefin layers are produced in a weight ratio of 20:80 to 50:50, the joined part possesses ample adhesive strength and yet permits ready peeling.

What is claimed is:

1. A package, comprising:
   a sheetlike lid having a hot melt layer;
   a tray member on which the hot melt layer of said lid is superposed, wherein said tray member is provided along the edge of a recess opening therein with a sheetlike flange part, and said tray member and said sheetlike lid are heat sealed at said sheetlike flange part, the heat sealed portion formed between said sheetlike flange part of said tray member and said sheetlike lid comprising at least one primary joined portion having one of said sheetlike parts strongly pressed down and partially buried in the other sheetlike part, and at least one secondary joined portion adjacent said primary joined portion having said sheetlike parts pressed down less strongly against each other than in said primary joined portion and at least on the inner side of said primary joined portion relative to the tray member in the direction of the cross section of said heat sealed portion for protecting said primary joined portion, wherein the distance from the edge of the inside surface of the wall of said tray member forming said recess opening, to the inner edge of said primary joined portion is at least 0.5 mm, and the width of said secondary joined portion is in the range of 0.1 to 10 mm.

2. A package according to claim 1, wherein two secondary joined portions are formed one each on opposite sides of said primary joined portion.

3. A package according to claim 1, wherein only one primary joined portion is formed.

4. A package according to claim 3, wherein two secondary joined portions are formed one each on opposite sides of said one primary joined portion.

5. A package according to claim 1, wherein said sheetlike lid is buried into said sheetlike flange part of said tray member.

6. A package according to claim 1, wherein said buried portion has a depth of at least 0.05 mm.

7. A package according to claim 2, wherein the partially buried part of said primary joined portion has a depth in the range of 0.1 to 0.4 mm.

8. A package according to claim 7, wherein the distance from the edge of the inside surface of the wall of said tray member forming said recess opening, to the inner edge of said primary joined portion is at least 1 mm.

9. A package according to claim 1, wherein two primary joined portions are formed parallelly to each other.

10. A package according to claim 9, wherein said hot melt layer is superposed or deposited on said sheetlike lid.

11. A package according to claim 1, wherein said tray member is formed of a laminated sheet comprising a layer of polyolefin, an intermediate layer impervious to gas and steam, and another layer of polyolefin, said lid is formed of a laminated sheet comprising of a layer of polyamide, a layer impervious to gas and steam, and a layer resistant to the heat of heat sealing, in the order mentioned, and said hot melt layer is superposed or spread on the polyamide layer side.

12. A package according to claim 11, wherein the polyolefin layer in the laminated sheet of said tray member facing said lid is formed of polypropylene and said hot melt layer is formed of a blend of polyethylene and polypropylene.

13. A package according to claim 1, wherein said lid is in a peelable state relative to said tray member.

* * * * *